United States Patent [19]

Wheeler

[11] Patent Number: 4,660,267
[45] Date of Patent: Apr. 28, 1987

[54] METHOD FOR FABRICATING AN ARTHROSCOPIC SHAVER

[75] Inventor: C. Ray Wheeler, St. Joseph, Mo.

[73] Assignee: Richards Medical Company, Memphis, Tenn.

[21] Appl. No.: 798,829

[22] Filed: Nov. 18, 1985

Related U.S. Application Data

[62] Division of Ser. No. 473,242, Mar. 8, 1983, Pat. No. 4,603,694.

[51] Int. Cl.[4] .................. B23P 11/00; B21D 53/10
[52] U.S. Cl. ................................ 29/437; 29/445; 29/149.5 R; 29/157 R; 384/246
[58] Field of Search .......... 29/434, 445, 437, 149.5 R, 29/157 R; 128/305, 312; 384/244, 246; 604/22

[56] References Cited

U.S. PATENT DOCUMENTS

| | | | |
|---|---|---|---|
| 3,844,272 | 10/1974 | Banko | 128/305 X |
| 4,011,869 | 3/1977 | Seiler, Jr. | 128/305 X |
| 4,111,207 | 9/1978 | Seiler, Jr. | 128/305 |
| 4,513,745 | 4/1985 | Amoils | 128/305 |

*Primary Examiner*—Howard N. Goldberg
*Assistant Examiner*—Ronald S. Wallace
*Attorney, Agent, or Firm*—Pravel, Gambrell, Hewitt & Kimball

[57] ABSTRACT

An improved surgical device and method for manufacturing the device are provided. The device is a high rotating speed arthroscopic probe shaver with bearing means that give superior longitudinal and radial support. Further, the outer tube of the probe shaver is swaged to fit very closely over the inner tube.

5 Claims, 7 Drawing Figures

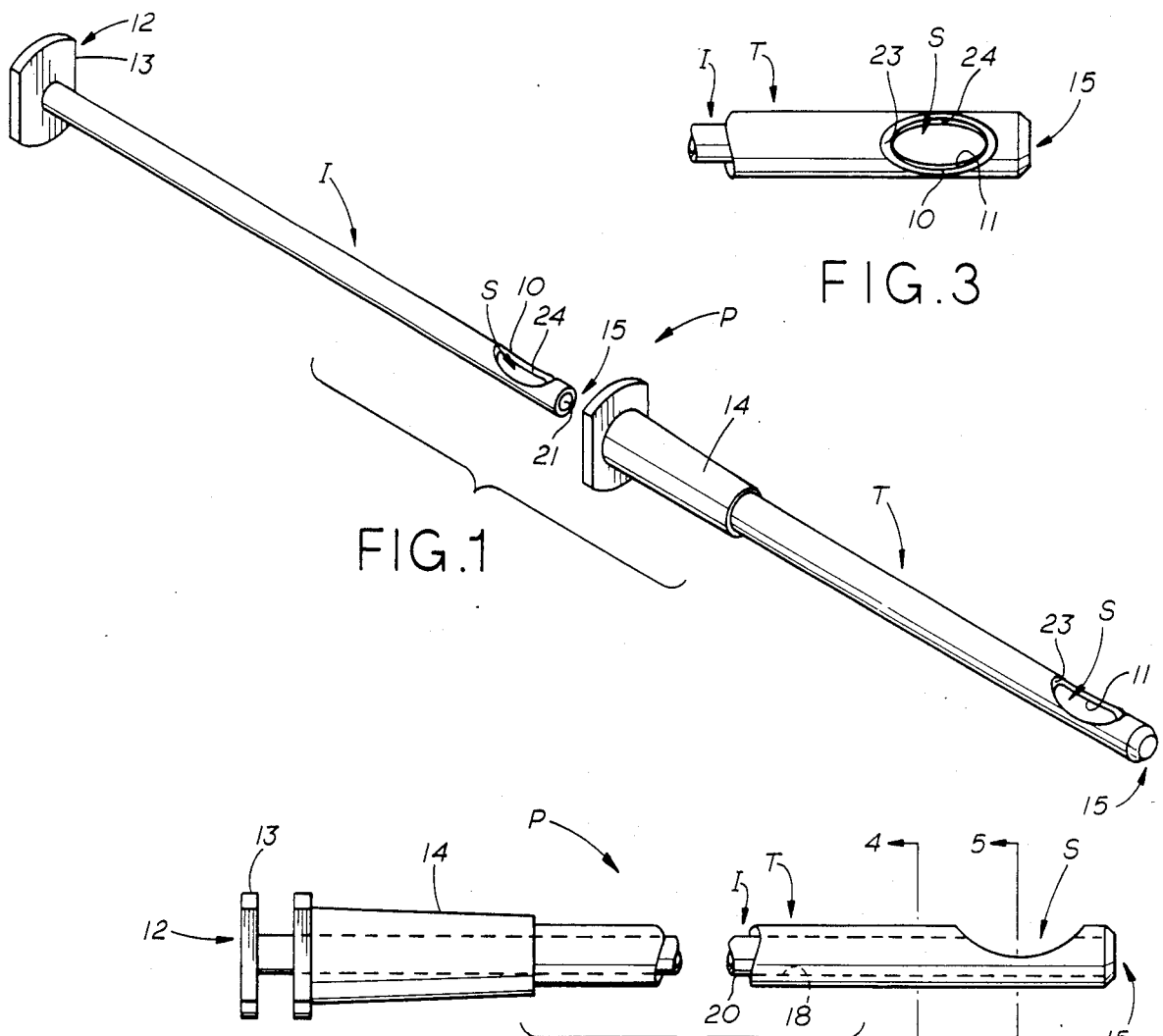

METHOD FOR FABRICATING AN ARTHROSCOPIC SHAVER

This is a division of application Ser. No. 473,242 filed Mar. 8, 1983, now U.S. Pat. No. 4,603,694 issued Aug. 5, 1986.

FIELD OF THE INVENTION

The present invention relates to surgical tools for cutting and removing tissue from the body. In particular, the present invention is useful for performing intra-articular surgery through arthroscopy without unnecessary surgery on the joint.

BACKGROUND OF THE INVENTION

Arthroscopy is becoming a popular method for removing diseased or damaged tissue from intra-articular regions of the body. Basically, arthroscopy is a method of surgery involving the use of probes for viewing and operating on regions of the body such as knee joints and other intra-articular regions. Its benefits arise from the smaller incisions involved which cause less scarring and heal more quickly than larger incisions required for other surgical techniques.

A variety of cutting devices have been developed for arthroscopy which include an outer tube sized and shaped for insertion through a puncture in the flesh with an inner tube adapted to rotate relative to the outer tube. These cutting devices typically have a side-facing opening through the inner and outer tubes into which tissue is drawn by a partial vacuum in the inner tube. As the inner tube rotates relative to the outer tube, the tissue drawn into the opening by the vacuum is cut off by the cutting interaction of the edges along the openings or of blades otherwise located in the instrument. This type of device is shown generally in U.S. Pat. Nos. 4,210,146; 4,203,444; 4,167,944; 3,996,935; 3,945,375; 3,844,272; and 3,618,611.

As surgeons gained greater experience with these devices, it became apparent that they operated better at higher rotating speeds. It was found that tissues tended to be cut in smaller pieces and less tearing of the tissues occurred at higher RPM's. At these higher operational speeds, bearings or other means for maintaining the alignment of the inner cutting member relative to the outer tube became increasingly more important.

Attempts to develop devices with improved alignment are described in several U.S. patents. For example, U.S. Pat. No. 4,203,444 shows radial bearing surfaces 33, 35 on each side of the cutting blade at the side-facing window at FIG. 4 and a ring 37 at FIG. 3 for journaling the inner tube within the outer tube. U.S. Pat. No. 3,996,935 shows a conical inner seat 75 at the end of the outer tube with the tip of the conical seat pointing outwardly at the axial centerline of the tube and a corresponding end portion on the inner cutting member with a conical exterior surface 78 at FIG. 7. U.S. Pat. No. 3,844,272, by the same inventor as U.S. Pat. No. 3,996,935, shows a similar conical seat arrangement at FIG. 18A. This arrangement requires that the cutting opening be located at a relatively great distance from the tip because of the length of the solid bar necessary to form the bearing, causing unnecessary tissue disturbance.

None of these devices is believed to have a satisfactory bearing arrangement for maintaining proper axial alignment during operations at higher speeds and under non-axial loading conditions.

SUMMARY OF THE INVENTION

The present invention is directed to an improved bearing arrangement which is useful for extending the life and dependability of a powered arthroscopic probe shaver of the type that includes an outer tube and an inner tube that rotates at relatively high speeds to cause shaving action along the edges of a side-facing opening near the distal end of the probe. The bearing includes a first bearing surface which extends inwardly from the distal end of the outer tube and a second complementary bearing surface on the distal end of the inner tube which overlaps and cooperates with the first bearing surface in an annular space between the first bearing surface and the inner side surface of the outer tube. It is found that this type of bearing configuration maintains the alignment of the inner and outer tubes in a manner that provides both radial and longitudinal thrust bearing support and significantly reduces wear between the inner side surface of the outer tube and the outer side surface of the inner tube. This relationship places the cutting opening closer to the distal end of the instrument than possible for other configurations and tends to minimize tissue disturbance during surgery.

The alignment of the inner and outer tubes can be further maintained by swaging the outer tube to fit closely over an inner tube which has a smooth outer surface.

BRIEF DESCRIPTION OF THE DRAWINGS

For a better understanding of the invention, reference may be had to the following description of an exemplary embodiment of the invention taken in conjunction with the accompanying drawings in which:

FIG. 1 is a perspective view of the improved arthroscopic probe shaver showing the inner tube withdrawn from the outer tube;

FIG. 2 is a side elevational view of the improved arthroscopic probe shaver with a cutaway showing the inner tube;

FIG. 3 is a top view of the distal end of the improved arthroscopic probe shaver;

FIG. 4 is a sectional view taken along the line 4—4 of FIG. 2;

FIG. 5 is a sectional view showing the side-facing opening taken along the line 5—5 in FIG. 2;

FIG. 6 is a side-sectional view of the distal end of the arthroscopic probe cutter showing the inner tube fully engaged with the outer tube; and FIG. 7 is a side-sectional view of the distal end of the inner tube with the distal end of the outer tube shown removed longitudinally.

DETAILED DESCRIPTION OF THE AN EMBODIMENT

An exemplary embodiment of the improved arthroscopic probe cutter of the present invention is described with reference to the drawings along with an improved method for manufacturing the probe. The improved arthroscopic probe cutter will be referred to in this specification generally by reference letter P.

As can be seen from the drawings, the probe P is elongate and otherwise sized and shaped for insertion through a puncture in the flesh of a body. The probe P is made up of an inner tube I and an outer tube T. The outside diameter of the inner tube I, which defines an outer side surface 20 of the inner tube I, is substantially equal to but slightly smaller than the inside diameter of the outer tube T which defines an inner side surface 18 of the outer tube T.

As shown in FIG. 4, the inner tube I fits into the outer tube T and the inner side surface 18 of the outer tube T is close to the outer side surface 20 of the inner tube T. The outer side surface 20 of the inner tube I and the inner side surface 18 of the outer tube T both have smooth finishes to reduce friction and allow the inner tube I to rotate relative to the outer tube T.

The probe P has proximal and distal ends which are generally designated as reference numerals 12, 15, respectively. The proximal end 12 is adapted for connection to a motor or other type of driving mechanism (not shown), through a proximal seat 14 formed on the outer tube T and a proximal connection 13 formed on the inner tube I. The connections 13, 14 are shaped so that they can engage the driver which operates to hold the outer tube T stationary while rotating the inner tube I to perform the arthroscopic operation. The configurations of the connectors 13, 14 are merely illustrative and others can be used to adapt the invention to different types of driving mechanism.

As shown in FIG. 1, both the inner tube I and the outer tube T have side-facing openings S near the distal end 15 of the probe P. The side-facing openings S co-act in a cutting or shaving action as described in greater detail below. The shaver operates to draw tissue (not shown) into the side-facing openings by creating a suction in the inner tube I in a conventional manner. Tissue sucked into the opening S is then cut in a compound scissor fashion as the inner tube I rotates relative to the outer tube T. The suction then draws the tissue shavings away from the distal end 15 of the probe P to avoid clogging of the opening S.

The side-facing opening S of the inner tube I is defined by a blade edge 10 and the opening of the outer tube T by a cooperating edge 11 which co-acts with the blade edge 10. As the inner tube I rotates, the blade edge 10 on the inner tube I moves past the cooperating edge 11 and the cooperating oval shaped openings slice the tissue at two points until it is completely cut off at the respective centers of the openings as they pass each other.

As shown in FIG. 5, the blade edge 10 of the inner tube I is formed with a blade surface 24 which is preferably formed at an angle to the vertical sufficient to form a sharp cutting edge. The cooperating edge 11 of the outer tube T is formed on a rim surface 23 which is substantially perpendicular to the inner surface 18 of the outer tube T. Further, the openings are formed so that the blade edges 10, 11 are elliptical in shape (see FIG. 3) with the widest part of the opening slightly above the centerline of the probe as shown in FIG. 5. As the inner tube I rotates and closes the ellipse of the stationary outer tube T, the elliptical or oval shape ensures that the cutting or shaving action will proceed longitudinally from the ends of the opening S toward the center. With oval or elliptical openings S, the highest cutting stress occurs at the center of the openings S rather than nearer the distal end 15 of the probe P as with openings of different shapes. It has been found that oval openings S provide a shaving or cutting action that is less prone to clogging of the opening. Openings of this shape also tend to minimize stresses in the tip of the cutting instrument.

As can be seen in FIGS. 6 and 7, the invention includes a unique bearing arrangement designated generally by the reference letter B at the distal end 15 of the probe P for supporting and aligning the inner tube I relative to the outer tube T. The bearing B includes a first bearing surface 16 which projects into the outer tube T and forms an annular space 17 (see FIG. 7) between the first bearing surface 16 and the inner side surface 18 of the outer tube T. A second bearing surface 19 is formed on the distal end 15 of the inner tube I, which is adapted to overlap and cooperate with the first bearing surface 16 in the annular space 17. The bearing B provides both radial and longitudinal thrust bearing support and maintains the alignment of the inner tube I relative to the outer tube T.

As shown in FIGS. 6 and 7, the first bearing surface 16 is formed on the outer conical surface of a truncated cone which projects into the distal end 15 of the outer tube T. The second bearing surface 19 is formed as a beveled surface which defines an opening 21 on the distal end 15 of the inner tube I, this surface overlapping and cooperating with the outer conical surface of the first bearing surface 16.

The first bearing surface 16 is formed on a plug 22 that is adapted to fit in the distal end 15 of the outer tube T which is open. The plug 22 is formed so that the inner end 26 defines a truncated cone with the outer conical surface defining the first bearing surface 16. The plug 22 is fitted into the distal end 15 of the outer tube T and connected to the outer tube T by brazing, welding, gluing, or other means known in the art.

An additional feature of the present invention which provides further support and alignment for the inner tube I relative to the outer tube T is that the outer tube T is swaged to fit closely over the inner tube I. It is found that a swaged outer tube T provides a superior fit for the inner tube I and outer tube T of the probe P and helps eliminate radial wear. Further, the outer side surface 20 of the inner tube I is polished to a smooth finish to reduce frictional drag between the tubes as they rotate.

The improved arthroscopic probe cutter of the present invention can be manufactured of any suitable non-corrosive material, but is preferably made of #303 or #304 stainless steel. In order to obtain the superior results as taught by the present invention, the probe P can be assembled according to the method described below.

The probe P is formed so that the inner side surface 18 of the outer tube T and the outer side surface 20 of the inner tube I are relatively smooth. This can be accomplished by polishing the outer surface of the inner tube to at least a 32 micro finish at some stage in the manufacturing process. The inner surface of the outer tube is normally smooth enough that it does not require additional treatment.

After the bearing assembly is formed and assembled as described above, the inner tube I is inserted into the outer tube T and the first bearing suface 16 is brought into contact with the second bearing surface 19. The probe P is then swaged to reduce the diameter of the outer tube and cause inner side surface 18 of the outer tube T to fit closely over the outer side surface 20 of the inner tube I. This is accomplished by using a swaging tool to apply pressure on the outer surface of the outer tube T. The fit should be tight enough to prevent undue play between the tubes, but loose enough to allow the inner tube I to rotate freely.

After the swaging step, the side-facing openings S are formed simultaneously by cutting them while the inner tube I is inserted into the outer tube T and the bearing means are engaged to assure that the openings S coincide. The openings can be machined by means well known in the art to form a rim surface 23 on the outer tube T that is generally perpendicular to inner side surface 18 of the outer tube T. The surface defining the opening of the inner tube I is beveled to form a cutting blade 24 as described above.

It will be appreciated that the improved arthroscopic probe shaver of the present invention will operate at rotating speeds of approximately 200 RPM or higher with considerably more reliability and less wear on the bearing surfaces than possible in the prior art. The location of bearing surfaces in the distal end of the probe with the configuration described above is believed to achieve superior results over those of the prior art. By swaging the outer tube and providing the close fit along the length of the tubes, an accurate axial alignment is provided which results in greater precision during the surgical procedure.

The foregoing disclosure and description of the invention are illustrative and explanatory, and various changes in the size, shape and materials, as well as in the details of the illustrated construction may be made without departing from the spirit of the invention.

I claim:

1. A method for manufacturing an improved surgical instrument for cutting tissue, the instrument being of the type which includes an outer tube sized and shaped for insertion through a puncture in the flesh of a body, the outer tube having a side-facing opening therein for the entrance of tissue to be cut, an inner tube fitted in the outer tube and adapted to rotate relative to the outer tube, the inner tube including a side-facing opening defining a blade adapted to coact in cutting action with a cooperating edge of the side-facing opening of the outer tube, the inner tube including a longitudinal opening on its proximal end adapted for connection to a vacuum for drawing fluid and cuttings into the openings and for drawing the fluid and cuttings through the instrument, and the inner and outer tubes being adapted for connection on their proximal ends to a drive motor for rotating the inner tube relative to the outer tube so that the blade on the inner tube is moved past the cooperating edge of the side-facing opening in the outer tube, the method comprising the steps of:

forming the inner and outer tubes with the inner tube having a relatively smooth outer side surface and the outer tube having a relatively smooth inner side surface;

assembling a bearing on the distal end of the outer tube to support and align the inner tube relative to the outer tube;

inserting the inner tube in the outer tube; and swaging the outer tube until the inner side surface of the outer tube closely fits over the outer side surface of the inner tube.

2. The method of claim 1, including the step of:

forming the side-facing openings by cutting them simultaneously while the inner tube is inserted in the outer tube.

3. The method of claim 2, including the steps of:

forming side-facing openings entirely above the axial centerline of the tubes so that the openings are oval in shape and the blade edge of the opening on the inner tube is coincidental with the cooperating edge of the opening on the outer tube; and beveling the surface defining the opening on the inner tube to form a cutting blade.

4. The method of claim 2, including the steps of:

forming a first bearing surface that projects into the outer tube and forms an annular space between the first bearing surface and the inner side surface of the outer tube; and forming a second bearing surface at the distal end of the inner tube so that the second bearing surface overlaps and cooperates with the first bearing surface.

5. The method of claim 4, including the steps of:

forming the first bearing surface on a plug in the shape of an outer conical surface of a truncated cone projecting into the distal end of the outer tube;

connecting the plug at the distal end of the outer tube; and beveling the distal end of the inner tube to overlap and cooperate with the outer conical surface of the first bearing surface.

* * * * *